United States Patent [19]

Callahan et al.

[11] Patent Number: 5,247,933

[45] Date of Patent: Sep. 28, 1993

[54] PHOTONIC IONIC CLOTH RADIO AMPLIFIER

[76] Inventors: Philip S. Callahan, 2016 NW. 27th St.; Harry Kornberg, 1352 NW. 61st Terr., both of Gainesville, Fla. 32605

[21] Appl. No.: 772,652

[22] Filed: Oct. 7, 1991

[51] Int. Cl.$^5$ ............................................. A61B 5/00
[52] U.S. Cl. .................................. 128/635; 128/734; 128/639
[58] Field of Search ............... 128/399, 400, 379, 849, 128/403, 889, 635, 639, 734

[56] References Cited

U.S. PATENT DOCUMENTS

| | | | |
|---|---|---|---|
| 407,673 | 7/1889 | Mellon | 361/224 |
| 497,822 | 5/1893 | Royer | 361/224 |
| 871,479 | 11/1907 | Cooper | 361/224 |
| 3,867,939 | 2/1975 | Moore et al. | 128/400 |
| 3,916,447 | 11/1975 | Thompson | 128/849 |
| 3,997,785 | 12/1976 | Callahan | 250/338 |
| 4,205,685 | 6/1980 | Yoshida | 128/399 |
| 4,834,079 | 5/1989 | Benckhuijsen | 128/379 |

OTHER PUBLICATIONS

Senior, *The Elusive Search for Electroanesthesia*, Medical Instrumentation, vol. 18, No. 1, pp. 86-87, (1984).
Callahan, *Studies on the Shootborer Hysipyia grandella (Zeller) (Lep., Pyraliadae). XIX, The Antenna of Insects as an Electromagnetic Sensory Organ*, Turrialba, vol. 23, No. 3, pp. 263-274, (1973).
Callahan, *Moth and Candle: The Candle Flame as a Sexual Mimic of the Coded Infrared Wavelengths from a Moth Sex Scent (Pheromone)*, Applied Optics, vol. 16, No. 12, pp. 3089-3096, (1977).
Callahan et al., *Mechanism of Attraction of the Lovebug, Plecia neartica, to Southern Highways: Further Evidence for the IR-Dielectric Waveguide Theory of Insect Olfaction*, Applied Optics, vol. 24, No. 8, pp. 1088-1093, (1985).
Callahan, *Dielectric Waveguide Modeling at 3.0 cm of the Antenna Sensille of the Lovebug, Plecia neartica Hardy*, Applied Optics, vol. 24, No. 8, pp. 1094-1097, (1985).
Callahan, *Treating the AIDS Virus as an Antenna*, 21st Century, pp. 26-31, (1989).
Callahan, *Nonlinear Infrared Coherent Radiation as an Energy Coupling Mechanism in Living Systems*, Molecular and Biological Physics of Living Systems, pp. 239-273, (1990).

*Primary Examiner*—Kyle L. Howell
*Assistant Examiner*—George Manuel
*Attorney, Agent, or Firm*—Sterne, Kessler, Goldstein & Fox

[57] ABSTRACT

A method and apparatus for detecting radio waves that propagate along the atmospheric boundary layer of human skin. This function is realized with the use of a photonic cloth constructed of flax and wool, soaked in a saline solution and air dried, and subsequently placed upon the human skin. The radio waves can then be monitored by connecting the photonic cloth via a set of probes to an oscilloscope.

12 Claims, 5 Drawing Sheets

PHOTONIC IONIC CLOTH RADIO AMPLIFIER

BACKGROUND OF THE INVENTION

1. Field of the Invention

The present invention relates generally to a method and apparatus for detecting the radio frequencies that propagate along the atmospheric boundary layer of human skin.

2. Discussion of Related Art

The present invention described herein is based on the early work of Snape, d'Arsonval, Rabinovitch, and Leduc. In particular, Snape pioneered the use of extremely low radio frequencies (ELF) as an anesthetic in dental extraction (Snape, J., On electricity as an anesthetic in dental extractions, Trans. Odont. Soc. Gr. Brit., pp. 287–312. (1869)). Subsequently, in 1890, Arsine d'Arsonval demonstrated that ELF pulsed electrical currents, ranging from 2500 Hz to 10,000 Hz, induced general anesthesia in humans. Similarly, in 1902, Leduc demonstrated that a pulsed electrical DC current applied to the central nervous system could effectively induce anesthesia. Robinovitch did extensive work in the area of electric analgesia sleep and resuscitation (Robinovitch, L. G., Electric Analgesia Sleep and Resuscitation Anesthesia (chap. XVI), ed. J. T. Gwatheny. D. Appleton & Co., New York, pp. 628–643 (1914)). More recently, Czaja demonstrated that treatment in the ELF frequency range enhances the immune system (Czaja, W., Comparative Studies of Electroanalgesia and Barbiturates, Polski Archivum Weterynaryjne, pp. 205–224 (1986)).

Between 1965 and 1973 applicant demonstrated that antennae sensilla on insects act as photonic waveguides to collect and transmit infrared frequencies. From this early research, applicant postulated that living systems (e.g., insect spines and plant fibers) also utilize the radio portion of the frequency spectrum to energize photons from radio and infrared emitting molecules. The requirement for detecting and or stimulating infrared and radio emissions from living systems is the ELF modulation of the organic and gaseous interface located at the waxy surface of the system. That is, living systems store coherent photon emissions from the external environment which become part of the self-organization of the living system. It has been demonstrated that ELF frequencies in living systems range from $10^3$ Hz in nerve action potentials to $10^{-2}$ Hz for physiological functions.

From this prior research, applicant has determined that radio waves in the ELF region of the radio spectrum are propagated along the atmospheric boundary layer of the human skin. ELF in the range of 800 Hz to 5200 Hz averaging 1000 Hz, with narrowband 10,000 Hz to 150,000 Hz sideband ELF radio signals are natural to the skin surface. The 700 Hz to 10,000 Hz region of the frequency spectrum is the region of so called radio "whistlers" (i.e. radio signals) from atmospheric lightning strikes around the world. It is this atmospheric electricity that modulates the frequencies from the atmospheric boundary layer of the skin. These modulation frequencies are equivalent to the 3 Hz to 10 Hz oscillations discovered by Schumann stimulated by lightning. These flicker modulations (which are approximately 3 Hz to 6 Hz) can be observed on an oscilloscope while measuring the 1000 Hz and 10,000 sidebands present on the human skin.

FIGS. 1, 2 and 3 of the appended drawings are readings of an oscilloscope showing the radio signals in the 700 Hz to 10,000 Hz portion of the ELF radio spectrum that are emitted from normal, healthy human skin. These signals were detected by touching the oscilloscope probe to the photonic ionic cloth radio amplifier and touching the face of a cathode ray tube with the hand. A battery (DC) operated 222 Tektronix hand held digital storage oscilloscope and capacitance coupling, with no AC interference, was used for detecting these frequencies in this manner. At a 5 mV range and a 1 mS sweep time the amplitude ranges from ½ mV (weak signal) to 30 Mv (strong signal).

The oscilloscope sweep shown in FIG. 1 has approximately two main 1000 Hz frequencies (between approximately 800–1200 Hz), shown at $C_1$ and $D_1$, which are 180° out of phase and occur exactly 8.4 Ms apart. At high amplitudes the two main broad band frequencies generate a series of narrow sidebands of approximately 10,000 Hz, shown in FIG. 1 between $A_1$ and $B_1$. The 10,000 Hz sidebands are emitted when the two main 1000 Hz frequencies reach an amplitude of 15 Mv or higher. As shown in FIG. 2, there may be as few as one sideband, as shown at $A_2$, to as many as fifteen sidebands. At extremely high amplitudes there is a main band frequency splitting. As few as one sideband to as many as eight sidebands emit from the region of the 1000 Hz signal under such high amplitude conditions. FIG. 3 shows an example of an oscilloscope sweep at an extremely high amplitude, having two sidebands, shown at $A_3$ and $B_3$.

BRIEF DESCRIPTION OF THE INVENTION

These and other advances concerning electricity and its effect upon living systems, as well as the discovery that radio waves in the ELF region are propagated along the atmospheric boundary layer of the human skin are utilized by the present invention. The present invention includes a method and apparatus for detecting the radio frequencies that propagate along the atmospheric boundary layer of the human skin. This function is realized with the use of a photonic cloth constructed of flax and wool which is soaked in a saline solution and air dried, and subsequently placed upon the human skin. When the photonic cloth is placed in contact with the skin it has an electroanesthesic effect on the body.

BRIEF DESCRIPTION OF THE DRAWING AND SPECTRUM

The foregoing and other objects, features and advantages of the invention will be apparent from the following more particular description of the preferred embodiments of the invention, as illustrated in the accompanying drawings in which.

DESCRIPTION OF THE PREFERRED EMBODIMENTS

Figure 1:
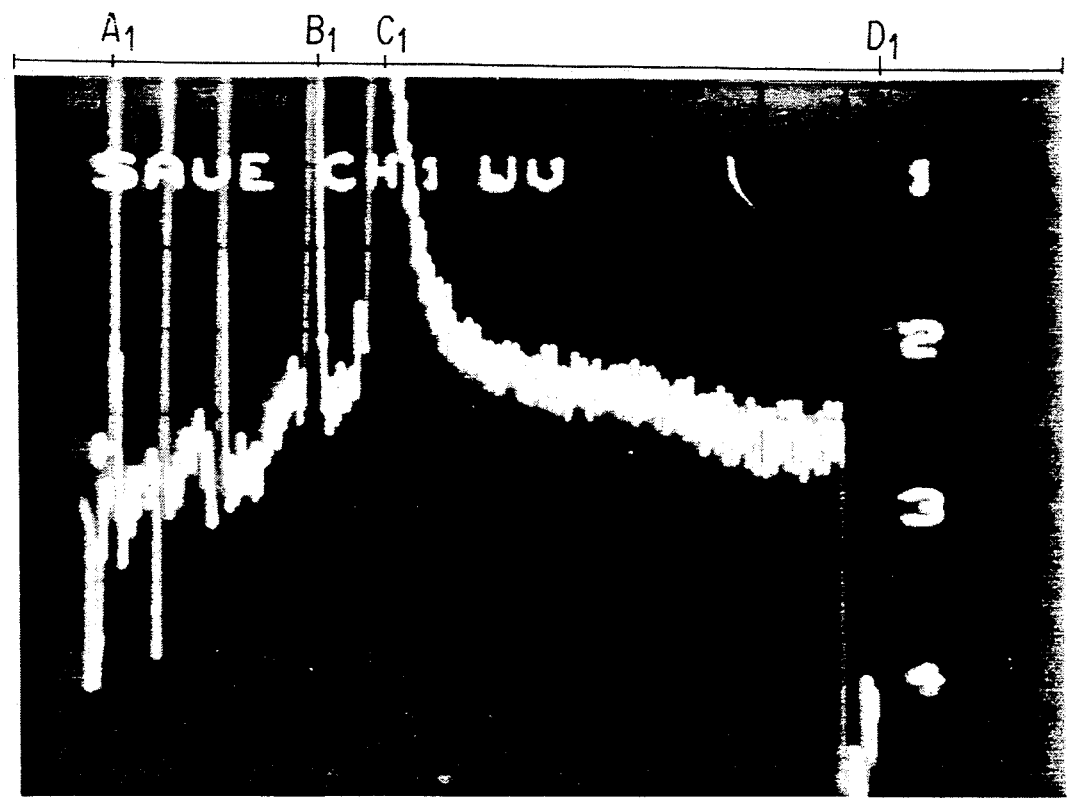
FIG. 1 is an oscilloscope recording showing the ELF radio signals that are emitted from normal human skin.
Figure 2:
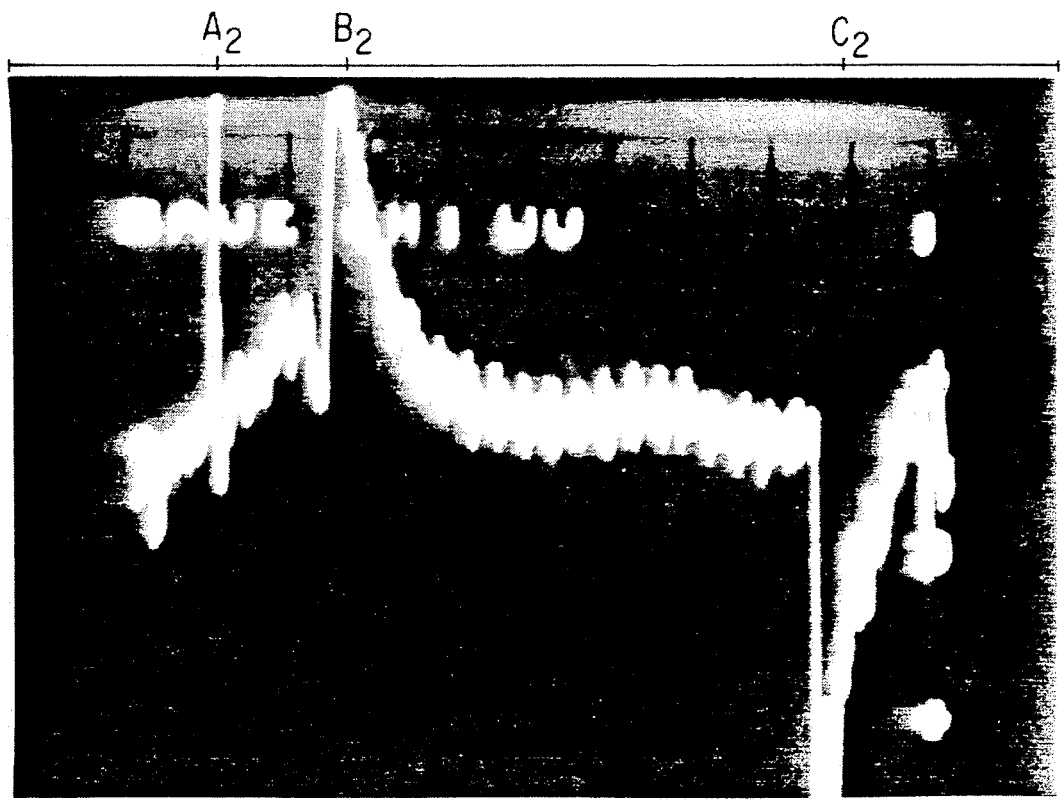
FIG. 2 is an oscilloscope recording showing the potential for ELF radio frequencies to have a single sideband.
Figure 3:
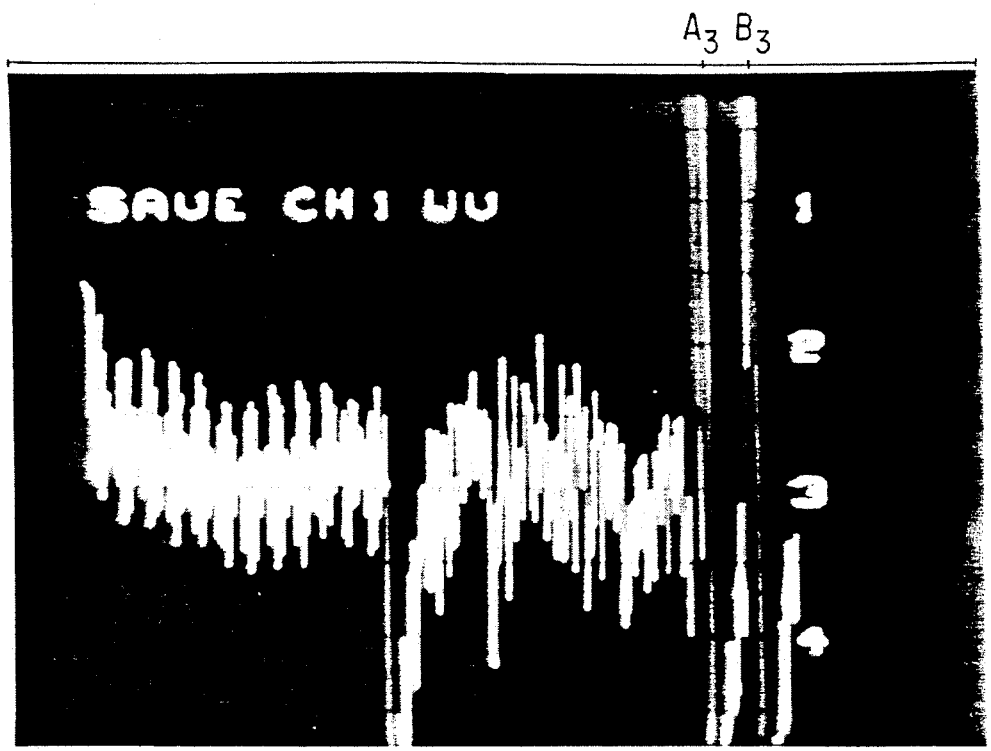
FIG. 3 is an oscilloscope recording showing the potential for ELF radio frequencies at extremely high amplitudes to have a single sideband.

As shown in FIGS. 1, 2 and 3, radio waves in the ELF region are propagated along the atmospheric boundary layer of the human skin. In particular, 1000 Hz (between approximately 800 Hz to 5200 Hz) and narrowband 10,000 Hz to 150,000 Hz sideband ELF radio signals are natural to the surface of the skin of the human body. The narrow sidebands vary from person to person (e.g., due to the health of the person), time of day and weather conditions, although the 1000 Hz and 10,000 Hz sidebands are continuously emitted from the skin's atmospheric boundary layer. The highest peak of these emissions occurs at dawn and dusk (i.e. between 0630 to 0930 hrs and from 1830 to 2130 hrs). The 1000 Hz and 10,000 Hz sideband frequencies can be detected, and amplified, by the photonic ionic cloth of the present invention.

Figure 4:
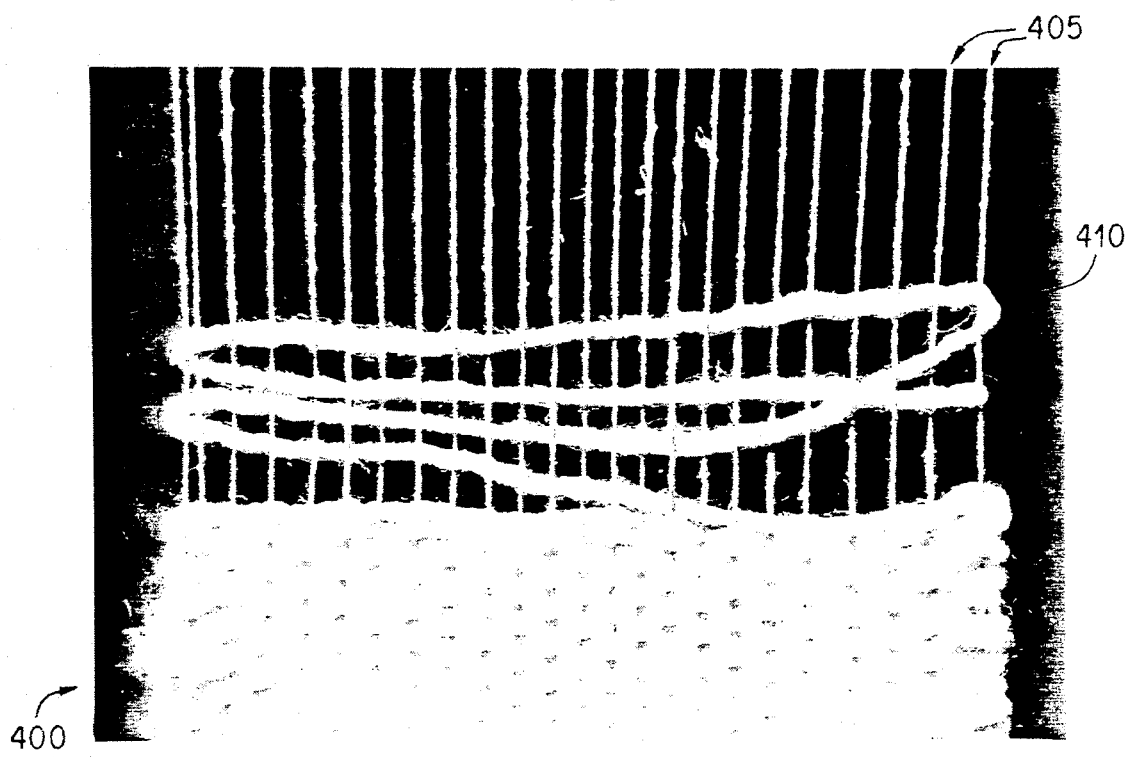
FIG. 4 is a perspective diagram of a woven photonic cloth of the present invention.

Referring to FIG. 4, one embodiment of the photonic cloth of the present invention is shown generally at 400. Photonic cloth 400 is constructed as a plain weave, comprising warp yarns 405 made of flax and weft or filling yarns 410 made of wool. Each warp yarn is a single yarn, while each filling yarn consists of three smaller yarns combined to form a single yarn. The flax used to form yarns 405 is natural and untreated (i.e., *Linum usitatissimum*). Similarly, weft yarns 410 should be made from natural, untreated wool. Thus, both the flax and wool should be unblended and unwashed so that the lanolin remains in the wool, and the waxy outer layer remains on the flax. The natural flax acts as a dielectric waveguide (i.e. it is photonic) due to its waxy characteristics. Although one yarn of flax is sufficient as warp yarns 405, experiments have shown that two or more yarns in combination will also detect and generate the 1000 Hz and 10,000 Hz sideband frequencies.

The photonic cloth can be any size. However, in the preferred embodiment of the present invention, cloth 400 is approximately two inch by six inch to six inch by fifteen inch. In the alternative, the cloth could be woven as a belt approximately three inch by forty-eight inch long.

In addition to weaving, the cloth could be knitted using any known technique utilizing natural and unblended flax as the warp yarns and natural and unblended wool for the filling.

To enhance the ability of the cloth to stimulate and/or detect the radio emissions from the skin surface, it is soaked in a saline solution for approximately one to six hours and then air dried until it is just slightly damp. The saline solution preferably consists of an isotonic aqueous solution containing a borate buffer system and sodium chloride, preserved with 0.1% of sorbic acid and disodium (EDTA). An alternative is to use four tablespoons of sea salt per ½ pint of water with the same borate buffer as described above. Ocean or sea water could also be used. The saline content in the damp cloth acts as an ionic detector for the radio energy emitted from the human skin. In particular, the hollow and fanshaped (i.e., branched) wool fibers act as an insulator, storing and feeding moisture to the waxy flax which absorbs the salt and thus becomes a photonic waveguide detector. Furthermore, the wool acts a condenser by keeping the system electrically charged above what it would be charged if the cloth was made of saline treated flax alone. Thus, the cloth should be kept slightly damp during use. In order to maintain this slight dampness, the cloth may be placed between two polyethylene layers or their equivalent and sealed to retain the slight moisture. It is important to maintain the cloth in a slightly damp condition, because if the cloth is completely dry or very damp the cloth will not function properly.

Figure 5:
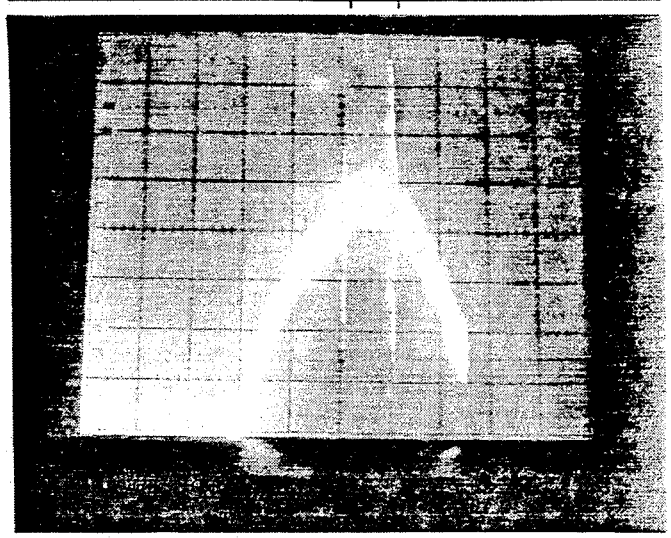
FIG. 5 is an oscilloscope recording taken from a piece of woven photonic cloth soaked in saline solution.
Figure 6:
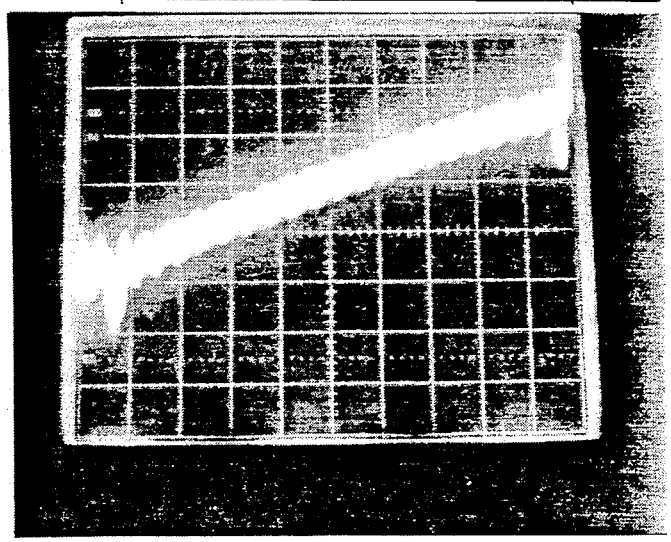
FIG. 6 is a magnification of the recording shown in FIG. 5.
Figure 7:
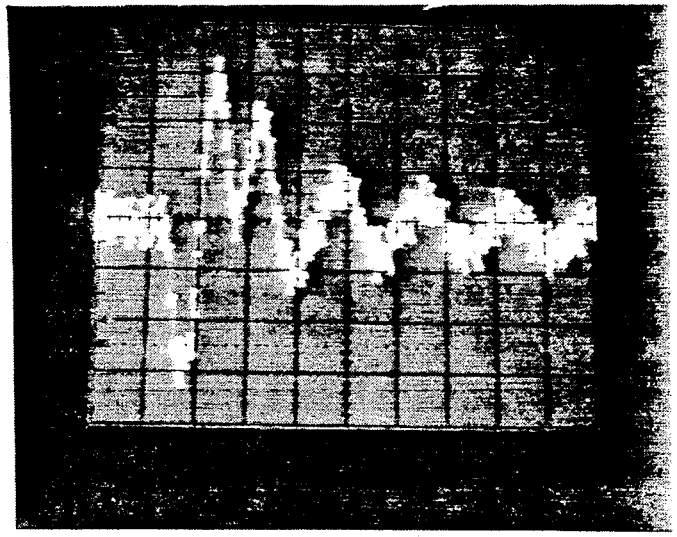
FIG. 7 is a magnification of the recording shown in FIG. 6 showing the details of the first 1000 Hz frequency.
Figure 8:
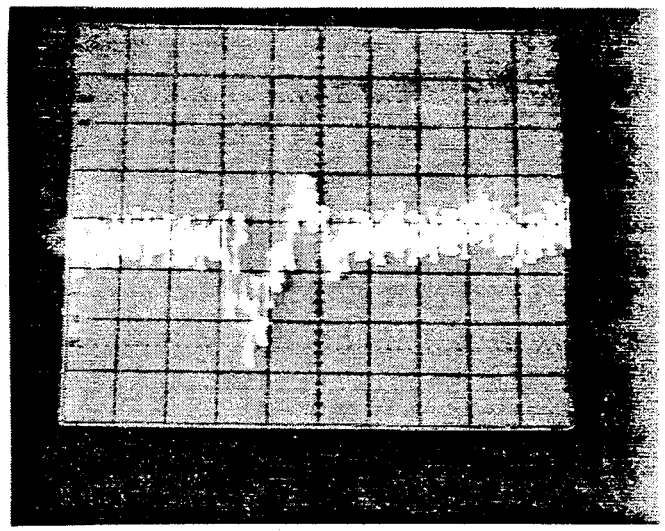
FIG. 8 is a magnification of the recording shown in FIG. 6 showing the details of the second 1000 Hz frequency.

Turning now to FIG. 5, an oscilloscope recording taken at 0702 from a piece of saline-soaked, air dried woven photonic cloth is shown. This reading was taken with a 2214 digital storage oscilloscope at 1× magnification and 10× amplitude. The woven photonic cloth was soaked in saline solution for three hours and dried for six hours. FIG. 5 shows two 1000 Hz frequencies, shown at $A_5$ and $B_5$, which are 8.4 Ms apart, and riding an AC interference. FIG. 6, which is a magnification of the recording shown in FIG. 5 (taken at 0710, at 10× magnification and 10× amplitude), shows the two 1000 Hz frequencies, shown at $A_6$ and $B_6$, with peak to peak separation. FIG. 7 is a magnification of the details of the first 1000 Hz frequency shown at $A_6$ in FIG. 6. The recording in FIG. 7 was taken at 0725 at 50× magnification and 10× amplitude. FIG. 8 is a magnification of the details of the second 1000 Hz frequency shown at $B_6$ in FIG. 6. The recording in FIG. 8 was taken at 0720 at 50× magnification and 10× amplification. The oscilloscope used to make the recording shown in FIGS. 5, 6, 7 and 8 was set at a 5 Mv range with a 1 Ms Sweep. The oscilloscope sweep shown in FIG. 8 demonstrates that the human body acts as an antenna to transmit the E field back and forth across space as an ELF radio wave. The ELF radio signals are capable of penetrating six layers of human skin (approximately ¼" each), two feet of stacked fabric, and 2" of solid rock, with no attenuation whatsoever.

Figure 9:
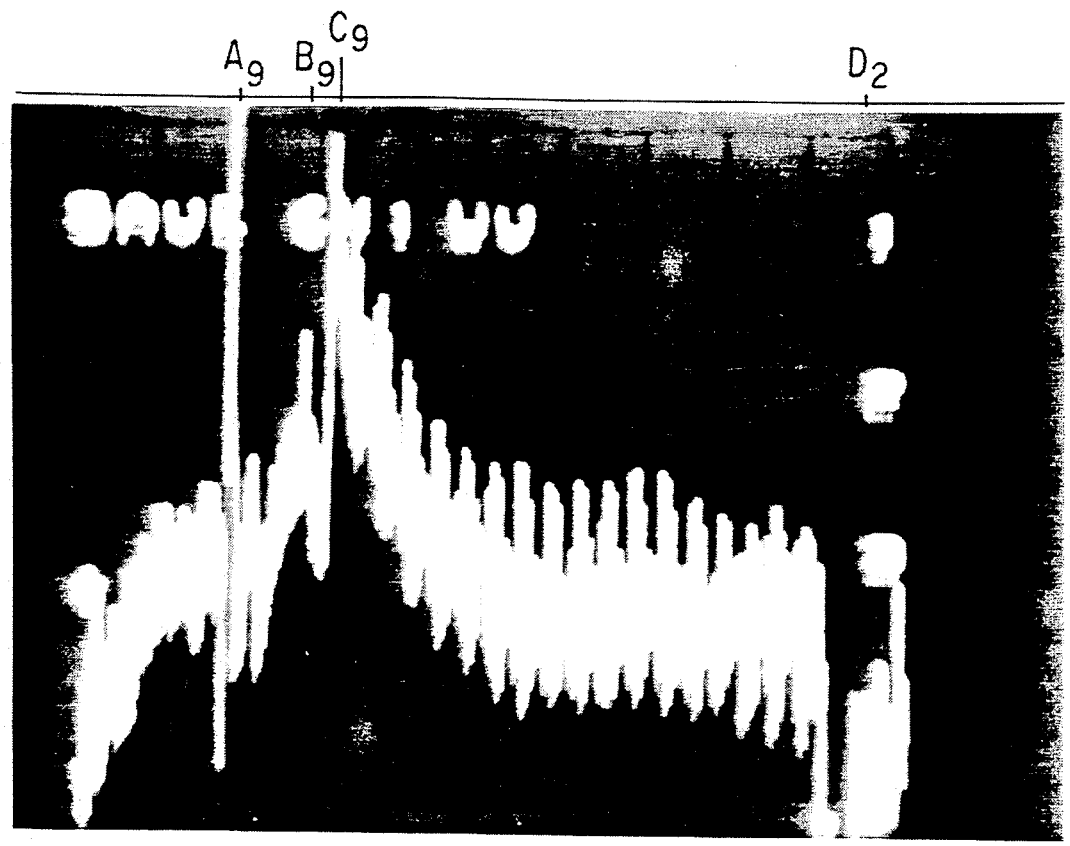
FIG. 9 is an oscilloscope recording taken from a 6 inch by 15 inch woven photonic cloth with the right hand of a lab assistant held approximately one foot from the cloth and the left thumb capacitance coupled to an oscilloscope.
Figure 10:
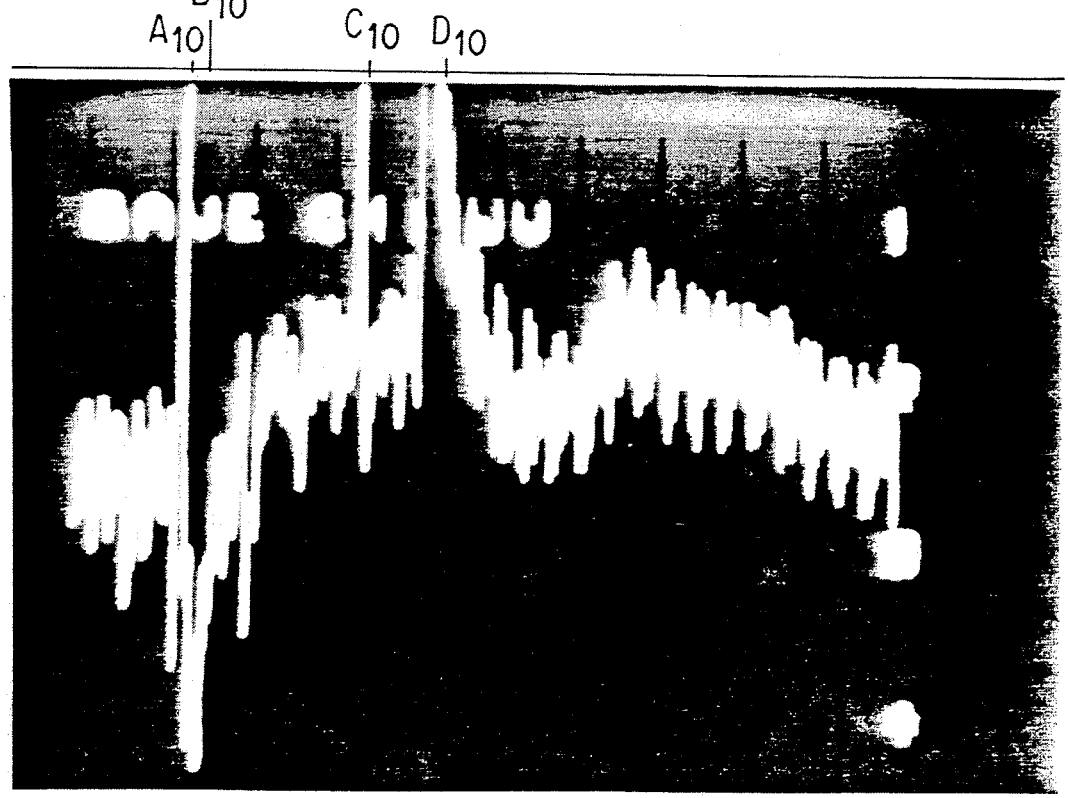
FIG. 10 is an oscilloscope recording taken from a 2 inch by 6 inch knitted photonic cloth with the left hand of a lab assistant touching the cloth and the right thumb capacitance coupled to the oscilloscope.

Referring now to FIG. 9, an oscilloscope sweep is shown which was taken from a six inch by fifteen inch sample of saline-soaked photonic woven cloth with one hand of a test person held approximately one foot from the photonic cloth and the thumb capacitance coupled to the 222 Tektronix digital storage oscilloscope at the cathode ray face. Two 1000 Hz frequencies are shown at $C_9$ and $D_9$ 8.4 Ms apart. Both 1000 Hz frequencies have two 10,000 Hz sidebands. An example of a pair of 10,000 Hz sidebands is shown at $A_9$ and $B_9$. Similarly, FIG. 10 shows an oscilloscope sweep taken from a two inch by six inch knitted piece of saline-soaked photonic cloth with the thumb capacitance coupled to the cathode ray face and the hand of the tester directly touching the cloth. The oscilloscope sweep shown in FIG. 10 demonstrates that with the body of the tester directly touching the photonic cloth, there is a tremendous increase in the amplitude of the 1000 Hz and 10,000 Hz sidebands signal, as opposed to the oscilloscope sweep shown in FIG. 9. The first main 1000 Hz signal shown at $B_{10}$ has one sideband signal of 10,000 Hz shown at $A_{10}$; the second main signal shown at $D_{10}$ also has one sideband signal of 10,000 Hz shown at $C_{10}$.

When the photonic cloth is placed against the human skin, the radio energy between the skin and the cloth are coherent. The photonic cloth has spacial coherence because the antenna aperture is zero. The 1 Ms sweep and fixed position of the waves demonstrate that there is temporal coherence as well. Furthermore, because the signal reaches an extremely high amplitude when the photonic cloth touches the skin, the signal also becomes a phase conjugated signal.

While the invention has been particularly shown and described with reference to preferred embodiments thereof, it will be understood by those skilled in the art that the foregoing and other changes in form and details may be made therein without departing from the spirit and scope of the invention.

What is claimed is:

1. An electrode for detecting bioelectric potentials comprising a cloth of untreated natural flax and untreated natural wool and soaked in a saline solution, which, when electrically coupled to a detector, will detect radio frequencies.

2. The electrode of claim 1, wherein said cloth is woven.

3. The electrode of claim 1, wherein said cloth is knitted.

4. The electrode of claim 1, further comprising two waterproof layers encompassing said soaked cloth to maintain said saline solution within said soaked cloth.

5. The electrode of claim 1, wherein said saline solution comprises:
   a borate buffer system;
   sodium chloride; and
   0.1% by weight of sorbic acid and disodium.

6. The electrode of claim 1, wherein said saline solution is sea water.

7. A photonic ionic electrode for detecting bioelectric potentials comprising a cloth of untreated natural flax combined with untreated natural wool to form the cloth, wherein the cloth is soaked in a saline solution.

8. The electrode of claim 7, wherein said untreated natural flax and said untreated natural wool are woven together.

9. The electrode of claim 7, further comprising two waterproof layers encompassing said soaked cloth to maintain said saline solution within said soaked cloth.

10. An apparatus for detecting radio frequencies, comprising: an electrode for detecting bioelectric potentials comprising a cloth constructed from untreated natural flax and untreated natural wool, wherein said cloth is soaked in a saline solution;
    a detector; and
    connection means for electrically connecting said cloth to said detector.

11. The apparatus of claim 10, wherein said cloth is woven.

12. The apparatus of claim 10, further comprising two waterproof layers encompassing said soaked cloth to maintain said saline solution within said soaked cloth.

* * * * *